United States Patent
Waki

(10) Patent No.: US 9,311,704 B2
(45) Date of Patent: Apr. 12, 2016

(54) ULTRASONIC DIAGNOSIS APPARATUS AND IMAGE DISPLAY METHOD

(71) Applicant: HITACHI ALOKA MEDICAL, LTD., Mitaka-shi, Tokyo (JP)

(72) Inventor: Koji Waki, Mitaka (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 0 days.

(21) Appl. No.: 14/435,551

(22) PCT Filed: Sep. 9, 2013

(86) PCT No.: PCT/JP2013/074271
§ 371 (c)(1),
(2) Date: Apr. 14, 2015

(87) PCT Pub. No.: WO2014/061370
PCT Pub. Date: Apr. 24, 2014

(65) Prior Publication Data
US 2015/0279025 A1  Oct. 1, 2015

(30) Foreign Application Priority Data

Oct. 18, 2012  (JP) .................................. 2012-230488

(51) Int. Cl.
*G06K 9/00* (2006.01)
*G06T 7/00* (2006.01)
(Continued)

(52) U.S. Cl.
CPC ............... *G06T 7/0012* (2013.01); *A61B 8/463* (2013.01); *A61B 8/485* (2013.01); *A61B 8/5207* (2013.01);
(Continued)

(58) Field of Classification Search
CPC ....................................................... G06T 11/00
USPC .................................................. 382/103, 131
See application file for complete search history.

(56) References Cited

U.S. PATENT DOCUMENTS

2007/0032726 A1  2/2007  Osaka et al.
2008/0103392 A1  5/2008  Seki et al.
(Continued)

FOREIGN PATENT DOCUMENTS

JP   2007-312958 A   12/2007
JP   2010-099292 A    5/2010
(Continued)

OTHER PUBLICATIONS

Oct. 8, 2013 International Search Report issued in International Patent Application No. PCT/JP2013/074271.

*Primary Examiner* — Stephen R Koziol
*Assistant Examiner* — Delomia L Gilliard
(74) *Attorney, Agent, or Firm* — Oliff PLC

(57) ABSTRACT

The ultrasonic diagnosis apparatus including a cross-section region image constituting unit configured to constitute a cross-section region image at a diagnosis portion of a diagnosing object through an ultrasound probe, an elasticity information calculating unit configured to calculate elasticity information indicating hardness, an elasticity image constituting unit configured to constitute an elasticity image based on the elasticity information calculated at the elasticity information calculating unit, and an image display unit configured to display the cross-section region image and the elasticity image, includes a temporal variation analyzing unit configured to analyze temporal variation at respective measurement points from the elasticity information calculated at the elasticity information calculating unit and a temporal variation image constituting unit configured to constitute a temporal variation image based on the temporal variation analyzed at the temporal variation analyzing unit, and the image display unit displays the temporal variation image.

14 Claims, 7 Drawing Sheets

(51) Int. Cl.
*A61B 8/08* (2006.01)
*G06K 9/46* (2006.01)
*G06K 9/52* (2006.01)
*G06T 11/60* (2006.01)
*A61B 8/00* (2006.01)

(52) U.S. Cl.
CPC ............... *A61B 8/5223* (2013.01); *G06K 9/46* (2013.01); *G06K 9/52* (2013.01); *G06T 11/60* (2013.01); *G06K 2009/4666* (2013.01); *G06T 2207/10132* (2013.01)

(56) References Cited

U.S. PATENT DOCUMENTS

| | | | |
|---|---|---|---|
| 2009/0149750 A1* | 6/2009 | Matsumura | A61B 5/0048 600/438 |
| 2011/0306884 A1* | 12/2011 | Tanigawa | A61B 8/463 600/443 |
| 2012/0253195 A1 | 10/2012 | Inoue et al. | |
| 2012/0321165 A1 | 12/2012 | Suda | |
| 2013/0114371 A1* | 5/2013 | Inoue | A61B 8/08 367/11 |
| 2013/0158400 A1* | 6/2013 | Inoue | A61B 8/463 600/438 |
| 2015/0087980 A1* | 3/2015 | Yao | A61B 8/463 600/440 |

FOREIGN PATENT DOCUMENTS

| | | |
|---|---|---|
| JP | 2010099292 A * | 5/2010 |
| WO | 2004/105615 A1 | 12/2004 |
| WO | 2006/013916 A1 | 2/2006 |
| WO | 2006/068079 A1 | 6/2006 |
| WO | 2009/072292 A1 | 6/2009 |
| WO | 2011/010626 A1 | 1/2011 |
| WO | 2011/102401 A1 | 8/2011 |

* cited by examiner

ULTRASONIC DIAGNOSIS APPARATUS AND IMAGE DISPLAY METHOD

TECHNICAL FIELD

The present invention relates to an ultrasonic diagnosis apparatus which displays a cross-section region image inside a diagnosing object by utilizing an ultrasonic wave, and an image display method.

BACKGROUND ART

An ultrasonic diagnosis apparatus transmits an ultrasonic wave to inside of a diagnosing object using an ultrasound probe, receives an ultrasound reflected echo signal according to a structure of biological tissue from the inside of the diagnosing object and constitutes and displays a cross-section region image of the inside of the diagnosing object.

Further, in the ultrasonic diagnosis apparatus, strain of tissue at a cross-section region portion of the diagnosing object is obtained, an elasticity image at the cross-section region portion is generated based on the strain and displayed on a display apparatus, a plurality of regions of interest are set in the cross-section region image displayed on the display apparatus or the elasticity image, elasticity information in each region of interest is indexed, and the index value is displayed at the display apparatus (see Patent Literature 1).

According to Patent Literature 1, it is possible to quantitatively evaluate hardness of biological tissue at a diagnosis portion.

CITATION LIST

Patent Literature

Patent Literature 1: WO 06/013916

SUMMARY OF INVENTION

Technical Problem

However, since an operator manually sets a plurality of regions of interest in a cross-section region image or an elasticity image, the calculated index value of the elasticity information depends on settings by the operator. Further, the operator cannot confirm whether measurement is performed while regions of interest are set at stable measurement positions.

Therefore, an object of the present invention is to provide an ultrasonic diagnosis apparatus which can display a temporal variation image based on temporal variation of elasticity information and an image display method.

Solution to Problem

To solve the above-described problem, in an ultrasonic diagnosis apparatus comprising a cross-section region image constituting unit configured to constitute a cross-section region image at a diagnosis portion of a diagnosing object through an ultrasound probe, an elasticity information calculating unit configured to calculate elasticity information indicating hardness, an elasticity image constituting unit configured to constitute an elasticity image based on the elasticity information calculated at the elasticity information calculating unit, and an image display unit configured to display the cross-section region image and the elasticity image, the ultrasonic diagnosis apparatus includes a temporal variation analyzing unit configured to analyze temporal variation at respective measurement points from the elasticity information calculated at the elasticity information calculating unit, and a temporal variation image constituting unit configured to constitute a temporal variation image based on the temporal variation analyzed at the temporal variation analyzing unit, and the image display unit displays the temporal variation image.

Further, an image display method for displaying a cross-section region image and an elasticity image, includes a step of analyzing temporal variation at respective measurement points from elasticity information indicating hardness, a step of constituting a temporal variation image based on the temporal variation, and a step of displaying the temporal variation image.

Advantageous Effect of Invention

According to the present invention, it is possible to display a temporal variation image based on temporal variation of elasticity information.

DESCRIPTION OF EMBODIMENTS

An ultrasonic diagnosis apparatus according to the present invention will be described below with reference to the drawings.

First Embodiment

Figure 1:
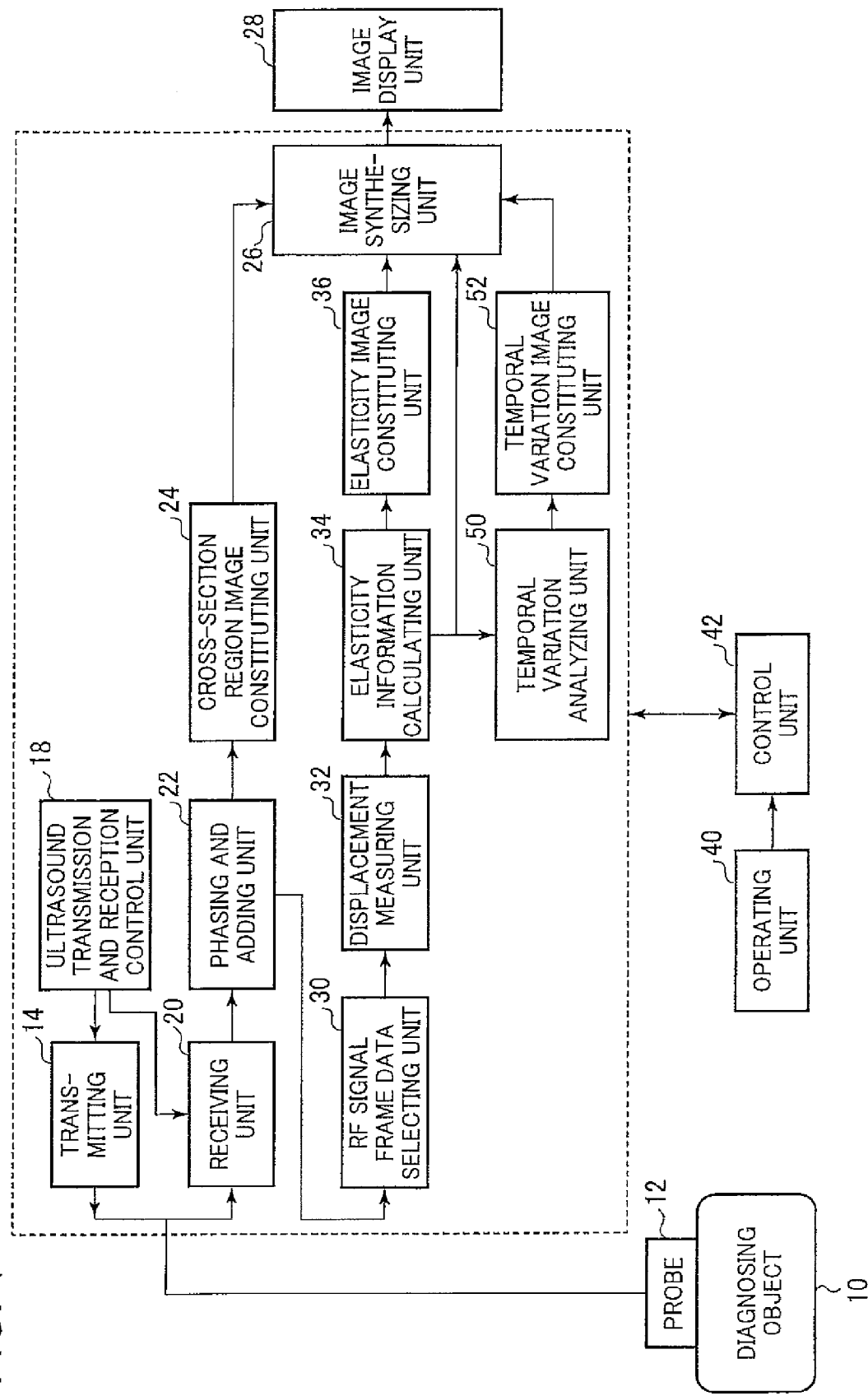
FIG. 1 is a block diagram illustrating a configuration of an ultrasonic diagnosis apparatus of the present invention.

FIG. 1 is a block diagram illustrating an ultrasonic diagnosis apparatus according to a first embodiment of the present invention.

As illustrated in FIG. 1, the ultrasonic diagnosis apparatus according to the present embodiment includes an ultrasound probe 12 used while being made to abut on a diagnosing object 10, a transmitting unit 14 configured to repeatedly transmit ultrasonic waves to the diagnosing object 10 through the ultrasound probe 12 at a time interval, a receiving unit 20 configured to receive time-series reflected echo signals generated at the diagnosing object 10, an ultrasonic wave transmission and reception control unit 18 configured to control the transmitting unit 14 and the receiving unit 20, a phasing and adding unit 22 configured to phase and add the received reflected echoes to generate RF signal frame data in a time-series manner, a cross-section region image constituting unit 24 configured to constitute a cross-section region image based on the RF signal frame data generated at the phasing and adding unit 22, an image synthesizing unit 26 configured to synthesize the cross-section region image, other images, numerical information, and the like, an image display unit 28 configured to display an image output from the image synthesizing unit 26, an RF signal frame data selecting unit 30 configured to select at least two pieces of RF signal frame data, a displacement measuring unit 32 configured to measure displacement of biological tissue of the diagnosing object 10 using the selected pieces of RF signal frame data, an elasticity information calculating unit 34 configured to obtain elasticity information from the displacement measured at the displacement measuring unit 32, an elasticity image constituting unit 36 configured to constitute an elasticity image from the elasticity information calculated at the elasticity information calculating unit 34, an operating unit 40 configured to allow an operator to perform operation, a control unit 42 configured to control respective components according to the operation at the operating unit 40, a temporal variation analyzing unit 50 configured to analyze temporal variation from the elasticity information calculated at the elasticity information calculating unit 34, and a temporal variation image constituting unit 52 configured to constitute a temporal variation image based on the temporal variation analyzed at the temporal variation analyzing unit 50. A dashed line illustrated in FIG. 1 indicates a body of the ultrasonic diagnosis apparatus.

The ultrasound probe 12 which is formed so that a plurality of transducers are arranged, transmits and receives ultrasonic waves to and from the diagnosing object 10 with which the ultrasound probe 12 is brought into contact, through the transducers. The transmitting unit 14 generates a transmission pulse for driving the ultrasound probe 12 to generate ultrasonic waves and sets a convergence point of ultrasonic waves to be transmitted at certain depth, and repeatedly transmits the ultrasonic waves to the diagnosing object 10 through the ultrasound probe 12 at a time interval. The receiving unit 20 has a function of receiving time-series reflected echo signals generated from the diagnosing object 10 through the ultrasound probe 12 and amplifying the received reflected echo signals with a predetermined gain to generate an RF signal (received signal). The ultrasonic wave reception control unit 18 controls the transmitting unit 14 and the receiving unit 20 to transmit and receive ultrasonic waves to the diagnosing object 10 through the ultrasound probe 12. The phasing and adding unit 22 phases and adds the reflected echo signals received at the receiving unit 20. At this time, the phasing and adding unit 22 performs phase control on the RF signal amplified at the receiving unit 20 to form an ultrasonic wave beam for one or a plurality of convergence points and generate time-series RF signal frame data which is ultrasonic wave cross-section region data.

The cross-section region image constituting unit 24 receives as input, data at a cross-section region portion of the diagnosing object 10, specifically, the RF signal frame data from the phasing and adding unit 22, performs signal processing such as gain correction, log compression, detection, contour enhancement and filtering processing to constitute cross-section region image data (for example, a monochrome gray-scale cross-section region image of the diagnosing object 10). Further, the cross-section region image constituting unit 24 is constituted to include an A/D converter configured to convert the cross-section region image data into a digital signal, a frame memory configured to store a plurality of pieces of converted cross-section region image data in a time-series manner, and a controller, which are not illustrated. The cross-section region image data of the inside of the diagnosing object 10 stored in the frame memory is acquired as one image, and the acquired cross-section region image data is read out in synchronization with TV.

The RF signal frame data selecting unit 30 stores the RF signal frame data output from the phasing and adding unit 22, and selects at least two pieces of (a pair of) RF signal frame data from the stored RF signal frame data group. For example, the RF signal frame data selecting unit 30 sequentially stores the RF signal frame data generated in a time-series manner from the phasing and adding unit 22, that is, based on a frame rate of an image, and selects the stored RF signal frame data (N) as first data, and selects one piece of RF signal frame data (X) from the RF signal frame data group (N-1, N-2, N-3, . . . , N-M) stored temporally in the past. It should be noted that N, M and X are index numbers assigned to the respective pieces of the RF signal frame data and are natural numbers.

The displacement measuring unit 32 measures displacement of the biological tissue of the diagnosing object 10. To be specific, the displacement measuring unit 32 obtains a vector indicating the displacement at the biological tissue corresponding to the respective measurement points of the cross-section region image, that is, one-dimensional or two-dimensional displacement distribution regarding direction and magnitude of the displacement from the pair of data selected by the RF signal frame data selecting unit 30, that is, the RF signal frame data (N) and the RF signal frame data (X) by performing one-dimensional or two-dimensional correlation processing. Here, a block matching method or a phase gradient method is used to detect the vector. In the block matching method, the image is divided into blocks comprised of, for example, N×N pixels, attention is focused on a block within a predetermined region (for example, a parameter acquisition region which will be described later), a block most approximate to the block on which attention is focused in a current frame is searched from the previous frame, and predictive coding, that is, processing for determining a sample value using a difference is performed with reference to the block. By this means, a vector is detected by obtaining displacement at the respective measurement points of the cross-section region image. In the phase gradient method, a vector is detected by calculating a movement amount of a wave of the received signal from phase information of the wave and obtaining displacement at the respective measurement points of the cross-section region image.

A pressure measuring unit which is not illustrated, measures stress at measurement points inside the diagnosing object 10 based on pressure detected by a pressure sensor, or the like, provided between an ultrasonic wave transmission and reception face of the ultrasound probe 12 and the diagnosing object 10.

The elasticity information calculating unit 34 obtains strain or a modulus of elasticity of tissue at the cross-section region portion based on the ultrasound cross-section region data at the cross-section region portion of the diagnosing object 10. In the present embodiment, the elasticity information calculating unit 34 calculates strain or a modulus of elasticity of the biological tissue corresponding to the respective measurement points on the cross-section region image based on displacement information of the biological tissue measured at the displacement measuring unit 32, for example, a motion vector, using the RF signal frame data selected by the RF signal frame data selecting unit 30. It should be noted that when calculating the modulus of elasticity of the biological tissue, the elasticity information calculating unit 34 takes into account a pressure value output from the pressure measuring unit.

At this time, data of the strain is calculated by spatially differentiating a movement amount, for example, displacement of the biological tissue. Further, data of the modulus of elasticity is calculated by dividing change of the pressure by change of the strain. For example, given that the displacement measured by the displacement measuring unit 32 is L(X) and the pressure measured by the pressure measuring unit is P(X), because strain ΔS(X) can be calculated by spatially differentiating L(X), strain ΔS(X) can be obtained using an equation of ΔS(X)=ΔL(X)/ΔX.

Further, a Young's modulus Ym(X) of the data of the modulus of elasticity can be obtained using an equation of Ym=ΔP(X)/ΔS(X). Because the modulus of elasticity of the biological tissue corresponding to the respective measurement points of the cross-section region image can be obtained from this Young's modulus Ym, two-dimensional elasticity image data can be continuously obtained. It should be noted that the Young's modulus is a ratio of simple tensile stress applied to an object with respect to strain occurring in parallel to tension.

The elasticity image constituting unit 36 constitutes an elasticity image at the cross-section region portion based on the elasticity information obtained at the elasticity information calculating unit 34. The elasticity image constituting unit 36 which is constituted to include a frame memory and an image processing unit, stores the elasticity frame data in the frame memory, and performs image processing on the stored frame data.

Further, the elasticity image constituting unit 36 has a function of providing hue information to the elasticity frame data, and converts the elasticity frame data into image data to which red (R), green (G) and blue (B) which are the three primary colors of light, are provided based on the elasticity frame data. For example, the elasticity image constituting unit 36 converts elasticity data including large strain into a red code, and converts elasticity data including small strain into a blue code.

The temporal variation analyzing unit 50 analyzes temporal variation at the respective measurement points (respective pixels) from the elasticity information calculated at the elasticity information calculating unit 34. The temporal variation analyzing unit 50 analyzes temporal variation at the respective measurement points from a plurality of frames of the elasticity information and calculates a measurement point at which temporal variation is greater than a threshold. The measurement point at which temporal variation is great is a measurement point where an index value of the elasticity information between the plurality of frames of the elasticity information is not stable (varies), and is a measurement point at which measurement cannot be performed using the index value of the elasticity information. The index value of the elasticity information is a value indexed using a ratio of the elasticity information, difference of the elasticity information, or the like.

The temporal variation image constituting unit 52 constitutes a temporal variation image indicating a degree of temporal variation based on the temporal variation analyzed at the temporal variation analyzing unit 50. The temporal variation image constituting unit 52 constitutes a temporal variation image for a measurement point at which temporal variation is greater than the threshold, while not constituting a temporal variation image for a measurement point at which temporal variation is smaller than the threshold.

The image synthesizing unit 26 which is constituted to include a frame memory, an image processing unit and an image selecting unit, creates a synthetic image of the cross-section region image and the elasticity image and a synthesis image of the cross-section region image and the temporal variation image using a method typified by a blending. The frame memory stores the cross-section region image data from the cross-section region image constituting unit 24, the elasticity image data from the elasticity image constituting unit 36 and the temporal variation image data from the temporal variation image constituting unit 52.

Further, the image processing unit synthesizes the cross-section region image data and the elasticity image data stored in the frame memory while changing a synthesis ratio, and synthesizes the cross-section region image data and the temporal variation image data stored in the frame memory while changing a synthesis ratio. Brightness information and hue information of each pixel of the synthetic images are obtained by adding respective information of the images to be synthesized at the respective synthesis ratios. Further, the image selecting unit selects an image to be displayed among the cross-section region image data, the elasticity image data and the temporal variation image data within the frame memory, and the synthetic image data in the image processing unit, and makes the image display unit 28 display the selected image.

It should be noted that the image synthesizing unit 26 is controlled by the control unit 42 based on image display conditions, or the like, set through the operating unit 40. The operating unit 40 includes operation devices such as a mouse, a keyboard, a track ball, a touch pen and a joystick, and can set the image display conditions, or the like.

The image display unit 28 displays the cross-section region image, the elasticity image, the temporal variation image, or the like, selected by the image selecting unit of the image synthesizing unit 26.

Figure 2:
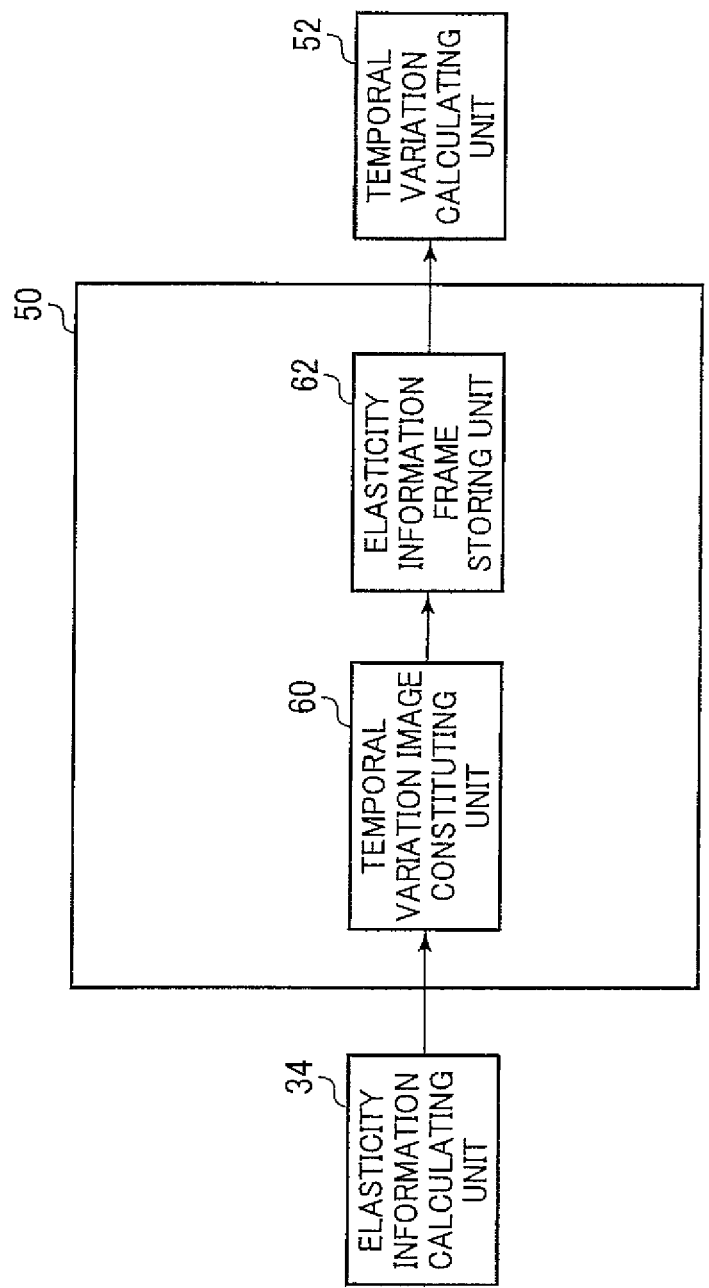
FIG. 2 is a block diagram illustrating a configuration of a temporal variation analyzing unit of the present invention.

Here, the temporal variation analyzing unit 50 will be described using FIG. 2. The temporal variation analyzing unit 50 has an elasticity information frame storing unit 60 configured to store a plurality of frames of the elasticity information, and a temporal variation calculating unit 62 configured to calculate temporal variation from the plurality of frames of the elasticity information.

The elasticity information calculating unit 34 obtains strain of the tissue at the respective measurement points at the cross-section region portion or the elasticity information of the modulus of elasticity for each frame based on the ultrasound cross-section region data of the cross-section region portion of the diagnosing object 10. The elasticity information frame storing unit 60 stores a plurality of frames of the elasticity information, for example, the elasticity information of ten frames, output from the elasticity information calculating unit 34. The number of frames stored in the elasticity information frame storing unit 60 can be set arbitrarily through the operating unit 40.

The number of frames to be stored in the elasticity information frame storing unit 60 can be also set in accordance with a compression cycle of the ultrasound probe 12. When the number of frames is set in accordance with the compression cycle of the ultrasound probe 12, the elasticity information frame storing unit 60 stores frames of the elasticity information corresponding to one cycle of compression.

Further, there is a method for deforming tissue using ultrasonic radiation pressure and measuring elasticity information from the displacement. The number of frames to be stored in the elasticity information frame storing unit 60 can be also set in accordance with exposure time of ultrasonic radiation pressure. When the number of frames is set in accordance with the exposure time of the ultrasonic radiation pressure, the elasticity information frame storing unit 60 stores frames of the elastic information being irradiated with ultrasound radiation pressure.

A calculation method of the temporal variation calculating unit 62 will be described using FIG. 3. As illustrated in the left side of FIG. 3, the image display unit 28 displays a synthetic image of the cross-section region image and the elasticity image. It should be noted that the image display unit 28 may display only the cross-section region image.

In the synthetic image of the cross-section region image and the elasticity image, in addition to normal tissue 70 and tumor tissue 72 which are morphologic information in the cross-section region image, sclerotic tissue 74 which is hardness information in the elasticity information is displayed while being superimposed on the tumor tissue 72 in the cross-section region image. Given that the tumor tissue 72 is displayed in black and the sclerotic tissue 74 is displayed in blue, a portion where the tumor tissue 72 is superimposed on the sclerotic tissue 74 is displayed in deep blue. The operator can observe a portion displayed in deep blue as a portion which is likely to be a malignant tumor.

The operator sets a region including the tumor tissue 72 as a region of interest 80 using the operating unit 40. Measurement points 82 are respectively set at respective measurement points (X1 to Xn, Y1 to Yn) in the synthetic image of the cross-section region image and the elasticity image. n is a natural number. The region of interest 80 is a region on which the operator focuses attention and is a region which is a target of comparison for a ratio of the elasticity information.

It is possible to make the region of interest 80 set at the operating unit 40 correspond to the plurality of frames of the elasticity information stored in the elasticity information frame storing unit 60. That is, it is possible to make a coordinate of the region of interest 80 set at the operating unit 40 correspond to coordinates of the plurality of frames of the elasticity information stored in the elasticity information frame storing unit 60. Therefore, the region of interest is set at the same position as the positions of the plurality of frames of the elasticity information.

The temporal variation calculating unit 62 makes the region of interest 80 set in the synthetic image of the cross-section region image and the elasticity image correspond to the plurality of frames of the elasticity information stored in the elasticity information frame storing unit 60. Then, the temporal variation calculating unit 62 respectively calculates the region of interest 80 set in the synthetic image of the cross-section region image and the elasticity image and the index value of the elasticity information at the respective measurement points 82 in the plurality of frames of the elasticity information. Here, description will be provided using an example of a ratio of the elasticity information as an index value of the elasticity information. The temporal variation calculating unit 62 calculates temporal variation at the respective measurement points based on the ratio of the elasticity information.

Figure 3:
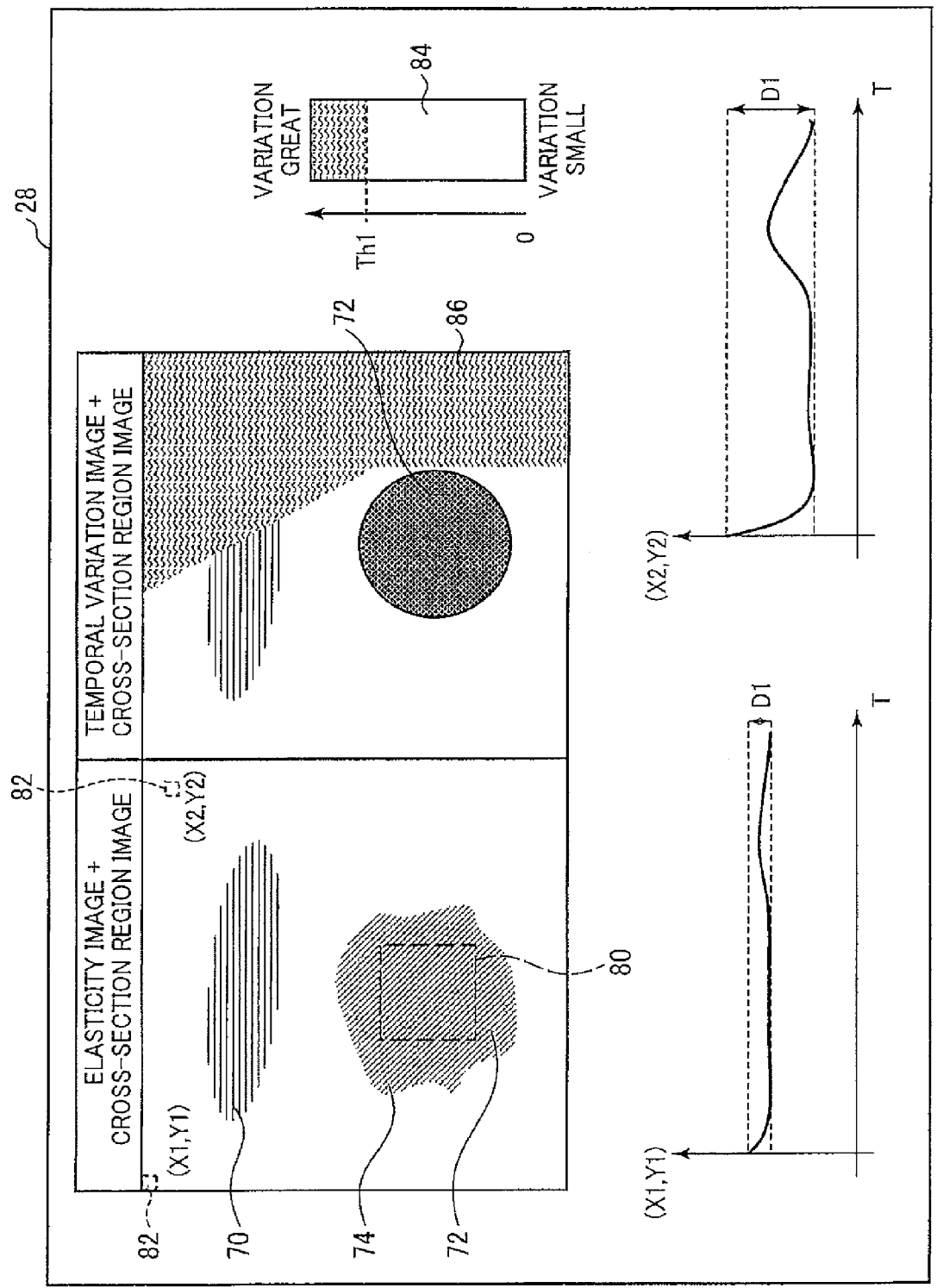
FIG. 3 is a diagram illustrating a display form of an image display unit of the present invention.

As illustrated in the lower side of FIG. 3, the image display unit 28 can also display temporal change of the ratio of the elasticity information at the respective measurement points using a graph. Here, description will be provided using an example of strain which is the elasticity information. The strain of the region of interest 80 is $\epsilon_1$, and the strain at the measurement points 82 is $\epsilon_2$. The strain $\epsilon_1$ of the region of interest 80 and the strain $\epsilon_2$ of the measurement points 82 are respectively average values of the strain in the respective regions. The temporal variation calculating unit 62 calculates a ratio of strain $\epsilon_2/\epsilon_1$ ($\epsilon_{ratio}$). The ratio of strain $\epsilon_2/\epsilon_1$ calculated at the temporal variation calculating unit 62 is displayed at the image display unit 28 along with the time. It should be noted that while description has been provided using an example of the strain of the elasticity information, parameters such as displacement, a modulus of elasticity and viscosity may be used.

Here, the temporal variation calculating unit 62 calculates variation of the index value of the elasticity information (ratio of the elasticity information) at the respective measurement points in the plurality of frames of the elasticity information. The temporal variation calculating unit 62 calculates a difference D1 between an upper limit value and a lower limit value of the ratio of the elasticity information at the respective measurement points in the plurality of frames of the elasticity information. When the difference D1 between the upper limit value and the lower limit value of the ratio of the elasticity information is greater than a predefined threshold Th1, the temporal variation calculating unit 62 calculates that the temporal variation is great. When the difference D1 between the upper limit value and the lower limit value of the ratio of the elasticity information is smaller than the predefined threshold Th1, the temporal variation calculating unit 62 calculates that the temporal variation is small.

Specifically, at the measurement points (X1, Y1), the difference D1 between the upper limit value and the lower limit value of the ratio of the elasticity information is smaller than the predefined threshold Th1, and variation of the ratio of the elasticity information is small. The temporal variation calculating unit 62 calculates that the measurement points (X1,Y1) are measurement points at which temporal variation is small. At the measurement points (X2, Y2), the difference D1 between the upper limit value and the lower limit value of the ratio of the elasticity information is greater than the predefined threshold Th1, and variation of the ratio of the elasticity information is great. The temporal variation calculating unit 62 calculates that the measurement points (X2, Y2) are measurement points at which temporal variation is great. In this way, the temporal variation calculating unit 62 compares the difference between the upper limit value and the lower limit value of the ratio of the elasticity information at the respective measurement points (X1 to Xn, Y1 to Yn) in the synthetic image of the cross-section region image and the elasticity image with the predefined threshold Th1 to calculate variation of the ratio of the elasticity information at the respective measurement points.

While the temporal variation calculating unit 62 calculates temporal variation using the difference between the upper limit value and the lower limit value of the ratio of the elasticity information at the respective measurement points, the temporal variation may be obtained using the following equation which uses standard deviation of the elasticity information in a time direction at the respective measurement points.

$$\partial_{xy} = \sqrt{\frac{\sum_{t=1}^{T}(\epsilon_{ratioxy}(t) - \bar{\epsilon}_{ratioxy})^2}{T}} \quad \text{[Equation 1]}$$

$\partial_{xy}$: time standard deviation at the respective measurement point $\epsilon_{ratioxy}$: a ratio of elasticity information at the respective measurement point $\bar{\epsilon}_{ratioxy}$: time average of a ratio of elasticity information at the respective measurement point T: time or frame Further, the temporal variation calculating unit 62 can use variance, a coefficient of variation, or the like, in place of the above. The temporal variation calculating unit 62 calculates temporal variation based on magnitude of dispersion of the elasticity information or calculates temporal variation based on magnitude of a coefficient of variation of the elasticity information.

As illustrated in the right side of FIG. 3, the temporal variation image constituting unit 52 constitutes a temporal variation image 86 indicating that temporal variation is greater than the threshold for the measurement point at which temporal variation analyzed at the temporal variation analyzing unit 50 is greater than the threshold. Specifically, the temporal variation image constituting unit 52 constitutes the temporal variation image 86 based on a temporal variation display bar 84 where measurement points at which temporal variation is greater than the threshold are identified.

The temporal variation display bar 84 is set so as to display the temporal variation image for the measurement points at which temporal variation is great. For example, the temporal variation display bar 84 is set so as to display the temporal variation image when the difference D1 between the upper limit value and the lower limit value of the ratio of the elasticity information is greater than the predefined threshold Th1 and not to display the temporal variation image when the difference D1 between the upper limit value and the lower limit value of the ratio of the elasticity information is smaller than the predefined threshold Th1.

That is, when the difference D1 between the upper limit value and the lower limit value of the ratio of the elasticity information is greater than the predefined threshold Th1, the temporal variation image constituting unit 52 constitutes a temporal variation image and makes the image display unit 28 display the temporal variation image. When the difference D1 between the upper limit value and the lower limit value of the ratio of the elasticity information is smaller than the predefined threshold Th1, the temporal variation image constituting unit 52 does not constitute a temporal variation image.

As illustrated in the right side of FIG. 3, the image display unit 28 displays a synthetic image of the cross-section region image and the temporal variation image. The operator can confirm that a region in which the temporal variation image is displayed is a region where there is temporal variation.

Another calculation method at the temporal variation calculating unit 62 will be described using FIG. 4. As illustrated in the left side of FIG. 4, the image display unit 28 displays a synthetic image of the cross-section region image and the elasticity image.

The operator sets a region of interest 90 using the operating unit 40. When the region of interest 90 is set, in the synthetic image of the cross-section region image and the elasticity image, in addition to the normal tissue 70 and the tumor tissue 72 which are morphologic information in the cross-section region image, sclerotic tissue 74 which is hardness information in the elasticity information is displayed while being superimposed on the tumor tissue 72 in the cross-section region image.

Measurement points 82 are respectively set at respective measurement points (Xa to Xm, Ya to Ym) in the region of interest 90 of the synthetic image of the cross-section region image and the elasticity image. a and m are natural numbers, and a<m.

The temporal variation calculating unit 62 calculates elasticity information in the set region of interest 90 and the measurement points 82 in a plurality of frames of the elasticity information stored in the elasticity information frame storing unit 60. The temporal variation calculating unit 62 calculates temporal variation at the respective measuring points based on displacement of the elasticity information.

Figure 4:
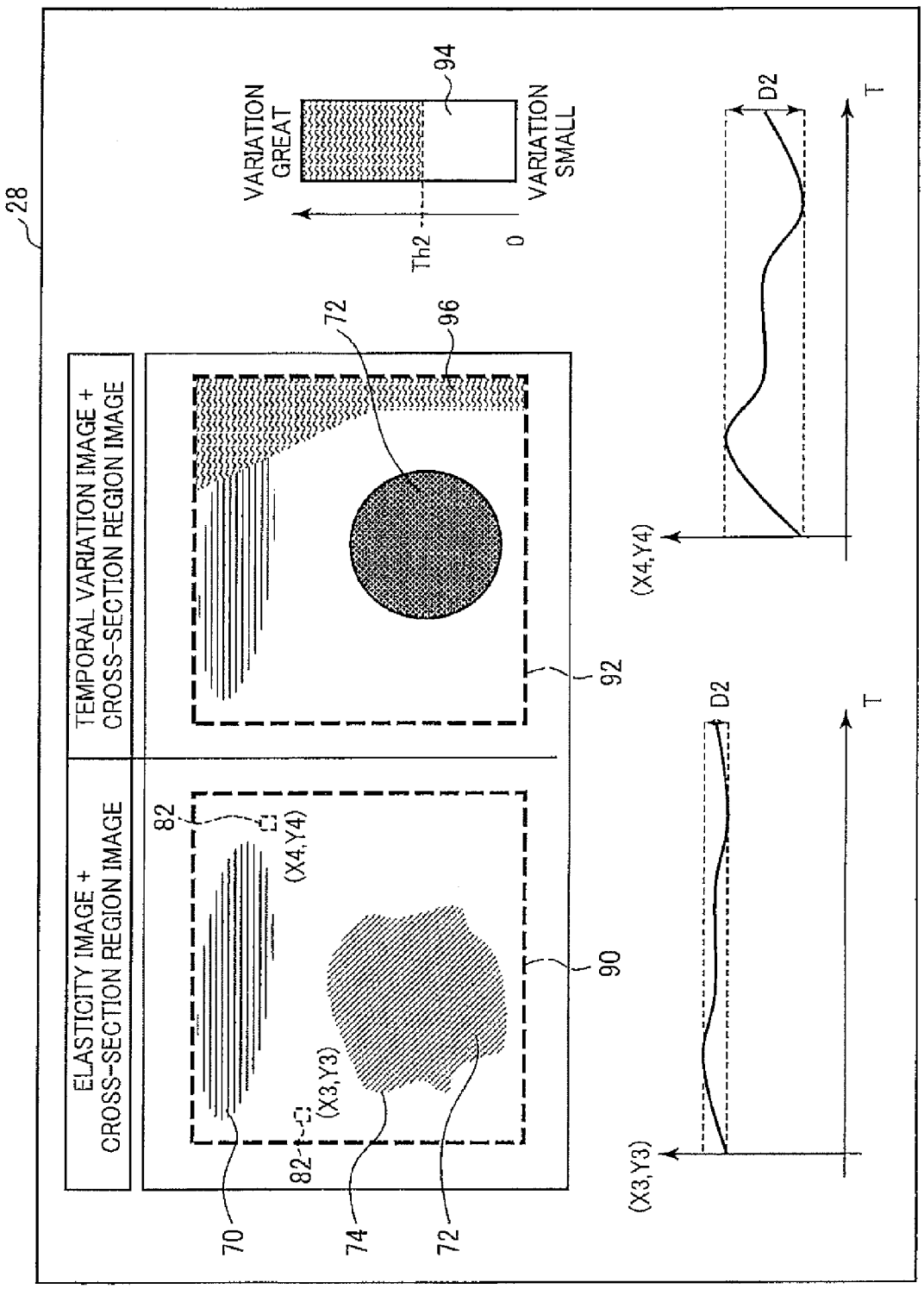
FIG. 4 is a diagram illustrating a display form of the image display unit of the present invention.

As illustrated in the lower side of FIG. 4, the image display unit 28 can also display the displacement of the elasticity information at the respective measurement points using a graph. Here, strain which is the elasticity information will be described as an example. The strain of the measurement points 82 is $\epsilon_3$. At the image display unit 28, the strain $\epsilon_3$ calculated at the temporal variation calculating unit 62 is displayed along with time. It should be noted that while an example of the strain of the elasticity information has been described, parameters such as displacement, a modulus of elasticity and viscosity may be used.

Here, the temporal variation calculating unit 62 calculates variation of the elasticity information at the respective measurement points in the plurality of frames of the elasticity information. The temporal variation calculating unit 62 calculates displacement D2 of the elasticity information at the respective measurement points in the plurality of frames of the elasticity information. When the displacement D2 of the elasticity information is greater than a predefined threshold Th2, the temporal variation calculating unit 62 calculates that temporal variation is great. When the displacement D2 of the elasticity information is smaller than the predefined threshold Th2, the temporal variation calculating unit 62 calculates that temporal variation is small.

Specifically, at the measurement points (X3, Y3), the displacement D2 of the elasticity information is smaller than the predefined threshold Th2, and the variation of the elasticity information is small. The temporal variation calculating unit 62 calculates that the measurement points (X3, Y3) are measurement points at which temporal variation is small. At the measurement points (X4, Y4), the displacement D2 of the elasticity information is greater than the predefined threshold Th2, and the variation of the elasticity information is great. The temporal variation calculating unit 62 calculates that the measurement points (X4, Y4) are measurement points at which temporal variation is great. In this way, the temporal variation calculating unit 62 compares the displacement of the elasticity information at the respective measurement points (Xa to Xm, Ya to Ym) in the region of interest 90 which is a display region of the elasticity image with the predefined threshold Th2 to calculate variation of the elasticity information at the respective measurement points.

As illustrated in the right side of FIG. 4, the temporal variation image constituting unit 52 constitutes a temporal variation image 96 indicating that the temporal variation is great for the measurement points at which the temporal variation analyzed at the temporal variation analyzing unit 50 is great. A display region 92 for displaying the temporal variation image 96 is the same region as the region of interest 90 which is displayed as the display region of the elasticity image.

Specifically, the temporal variation image constituting unit 52 constitutes the temporal variation image 96 based on a temporal variation display bar 94 where the measurement points at which the temporal variation is great are identified. The temporal variation display bar 94 is set so as to display the temporal variation image for the measurement points at which the temporal variation is great.

As illustrated in the right side of FIG. 4, the image display unit 28 displays a synthetic image of the cross-section region image and the temporal variation image. The operator can confirm that a region where the temporal variation image is displayed is a region where there is temporal variation.

Therefore, because the operator can recognize that the region where the temporal variation image is displayed is a region where there is temporal variation, the elasticity information calculating unit 34 can calculate an index value of the elasticity information in a region other than the region where the temporal variation image is displayed in the plurality of frames of the elasticity information stored in the elasticity information frame storing unit 60. Therefore, if the operator sets a region other than the region where the temporal variation image is displayed as a region of interest for which an index value of the elasticity information is calculated, it is possible to calculate an index value of the elasticity information without being affected by temporal variation. That is, it is possible to calculate an index value of the elasticity information at a stable measurement position.

It should be noted that when the temporal variation image is equal to or greater than a predetermined region (for example, equal to or greater than half of a screen) and it is inappropriate that the elasticity information calculating unit 34 calculates an index value of the elasticity information, the control unit 42 makes the image display unit 28 display an alarm for shooting an image again. When an image is shot again and the temporal variation image is smaller than the predetermined region (for example, smaller than the half of the screen), the control unit 42 regards that the elasticity image become stable, and the elasticity information calculating unit 34 calculates an index value of the elasticity information. The temporal variation image constituting unit 52 can also constitute a temporal variation image at the time when the image is shot again and make the image display unit 28 display the updated temporal variation image.

Figure 5:
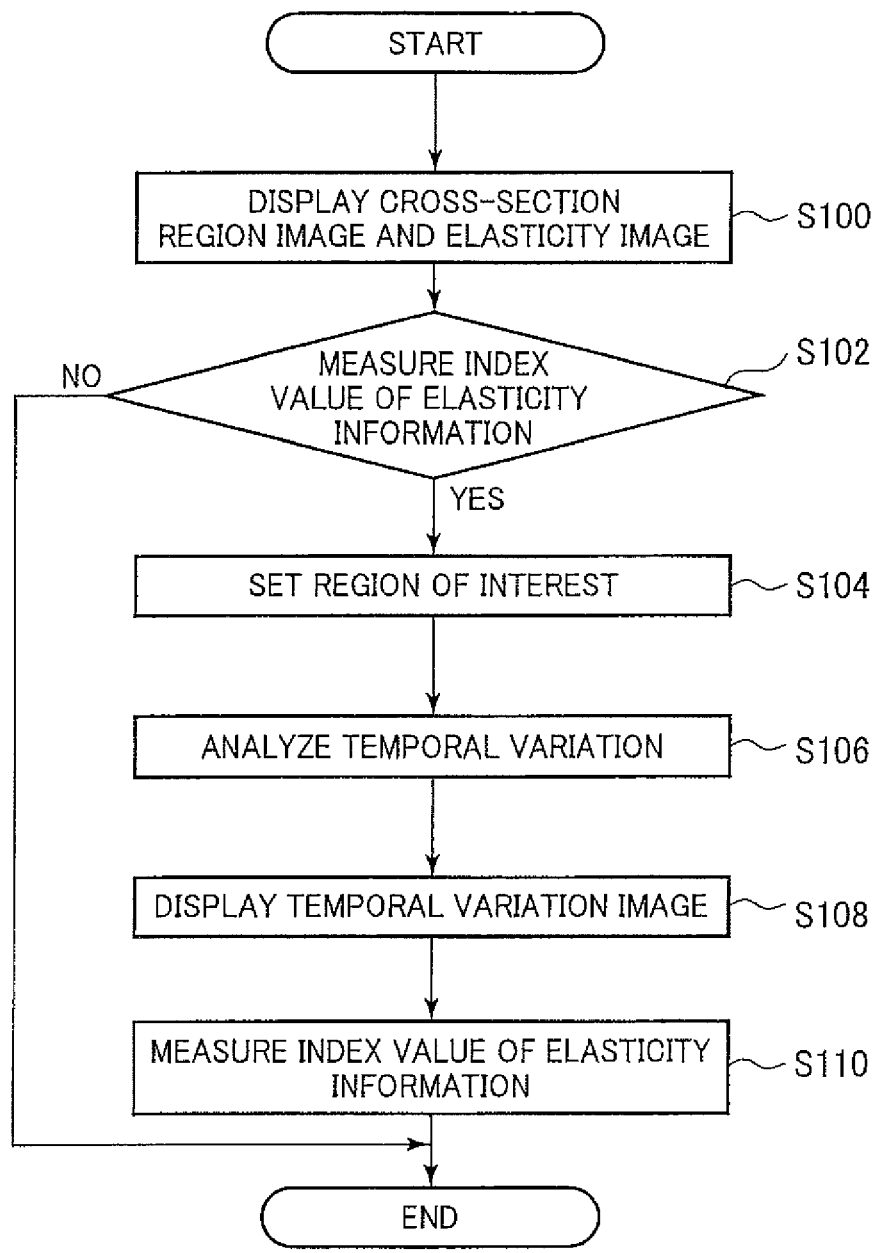
FIG. 5 is a flowchart illustrating operation of the present invention.

Operation of the present embodiment will be described next using FIG. 5.

(S100) The image display unit 28 displays a synthetic image of the cross-section region image constituted by the cross-section region image constituting unit 24 and the elasticity image based on strain or a modulus of elasticity, constituted by the elasticity image constituting unit 36.

(S102) It is selected whether or not an index value of the elasticity information is calculated at a predetermined measurement position on the synthetic image of the cross-section region image and the elasticity image. When the index value of the elasticity information is calculated, the flow proceeds to S104. When the index value of the elasticity information is not calculated, the flow ends.

(S104) The region of interest 80 is set using the operating unit 40. The region of interest 90 may be set as the display region of the elasticity image.

(S106) The temporal variation analyzing unit 50 calculates an index value or displacement of the elasticity information at the set region of interest and measurement points in the plurality of frames of the elasticity information. The temporal variation analyzing unit 50 compares the index value or the displacement of the elasticity information with a predefined threshold to calculate variation of the elasticity information at the respective measurement points.

(S108) The temporal variation image constituting unit 52 constitutes temporal variation images 86 and 96 indicating that the temporal variation is great for the measurement points at which the temporal variation analyzed at the temporal variation analyzing unit 50 is great.

(S110) The operator sets a region other than the region where the temporal variation image is displayed as a region of interest for which an index value of the elasticity information is calculated, and the elasticity information calculating unit 34 calculates an index value of the elasticity information.

It should be noted that the region of interest for which an index value of the elasticity information is calculated can be automatically set in a region other than the region where the temporal variation image is displayed. Specifically, the control unit 42 recognizes the region where the temporal variation image is displayed and sets a region other than the region where the temporal variation image is displayed as the region of interest. The control unit 42 sets sclerotic tissue 74 which is hardness information in the elasticity image in a region other than the region where the temporal variation image is displayed as a first region of interest, and sets a region other than the sclerotic tissue 74 and other than the region where the temporal variation image is displayed as a second region of interest. The elasticity information calculating unit 34 calculates an index value of the elasticity information (for example, a ratio of the elasticity information) in the first region of interest and the second region of interest set by the control unit 42 in the plurality of frames of the elasticity information stored in the elasticity information frame storing unit 60. The index value of the elasticity information calculated by the elasticity information calculating unit 34 is displayed at the image display unit 28 through the image synthesizing unit 26.

Further, the first region of interest and the second region of interest are set in advance through the operating unit 40, and when the temporal variation image constituted by the temporal variation image constituting unit 52 is superimposed on the first region of interest and the second region of interest, the elasticity information calculating unit 34 does not calculate an index value of the elasticity information in the first region of interest and the second region of interest. The control unit 42 makes the image display unit 28 display an alarm for shooting an image again. When the temporal variation image constituted by the temporal variation image constituting unit 52 is not superimposed on the first region of interest and the second region of interest, the elasticity information calculating unit 34 calculates an index value of the elasticity information in the first region of interest and the second region of interest. The index value of the elasticity information calculated by the elasticity information calculating unit 34 is displayed at the image display unit 28 through the image synthesizing unit 26.

As described above, according to the present embodiment, the ultrasonic diagnosis apparatus including the cross-section region image constituting unit 24 configured to constitute a cross-section region image of a diagnosis portion of the diagnosing object through the ultrasound probe 12, the elasticity information calculating unit 34 configured to calculate the elasticity information indicating hardness, the elasticity image constituting unit 36 configured to constitute the elasticity image based on the elasticity information calculated at the elasticity information calculating unit 34, and the image display unit 28 configured to display the cross-section region image and the elasticity image, further includes the temporal variation analyzing unit 50 configured to analyze temporal variation at the respective measurement points from the elasticity information calculated at the elasticity information calculating unit 34 and the temporal variation image constituting unit 52 configured to constitute a temporal variation image based on the temporal variation analyzed at the temporal variation analyzing unit, and the image display unit 28 displays the temporal variation image.

It is therefore possible to display the temporal variation image based on the temporal variation of the elasticity information. Further, it is possible to calculate an index value of the elasticity information at a stable measurement position in a region other than the region where the temporal variation image is displayed. That is, it is possible to calculate an index value of the elasticity information at a stable measurement position without depending on the operator.

Second Embodiment

Figure 6:
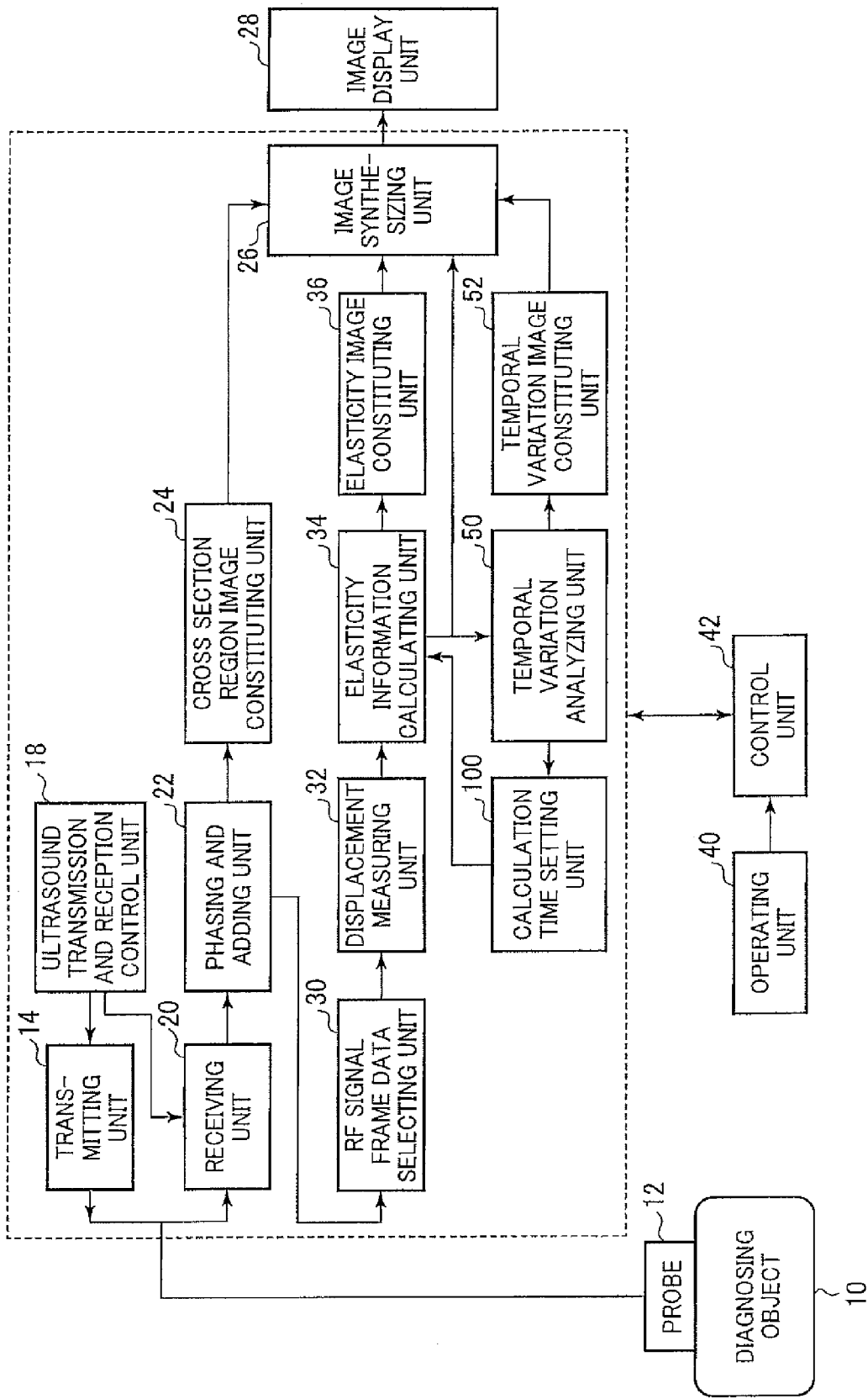
FIG. 6 is a block diagram illustrating a configuration of an ultrasonic diagnosis apparatus of the present invention.

A second embodiment will be described using FIG. 6 and FIG. 7. As illustrated in FIG. 6, the second embodiment is different from the first embodiment in that a calculation time setting unit 100 for setting a calculation time during which an index value of the elasticity information is calculated by the elasticity information calculating unit 34 is provided.

Figure 7:
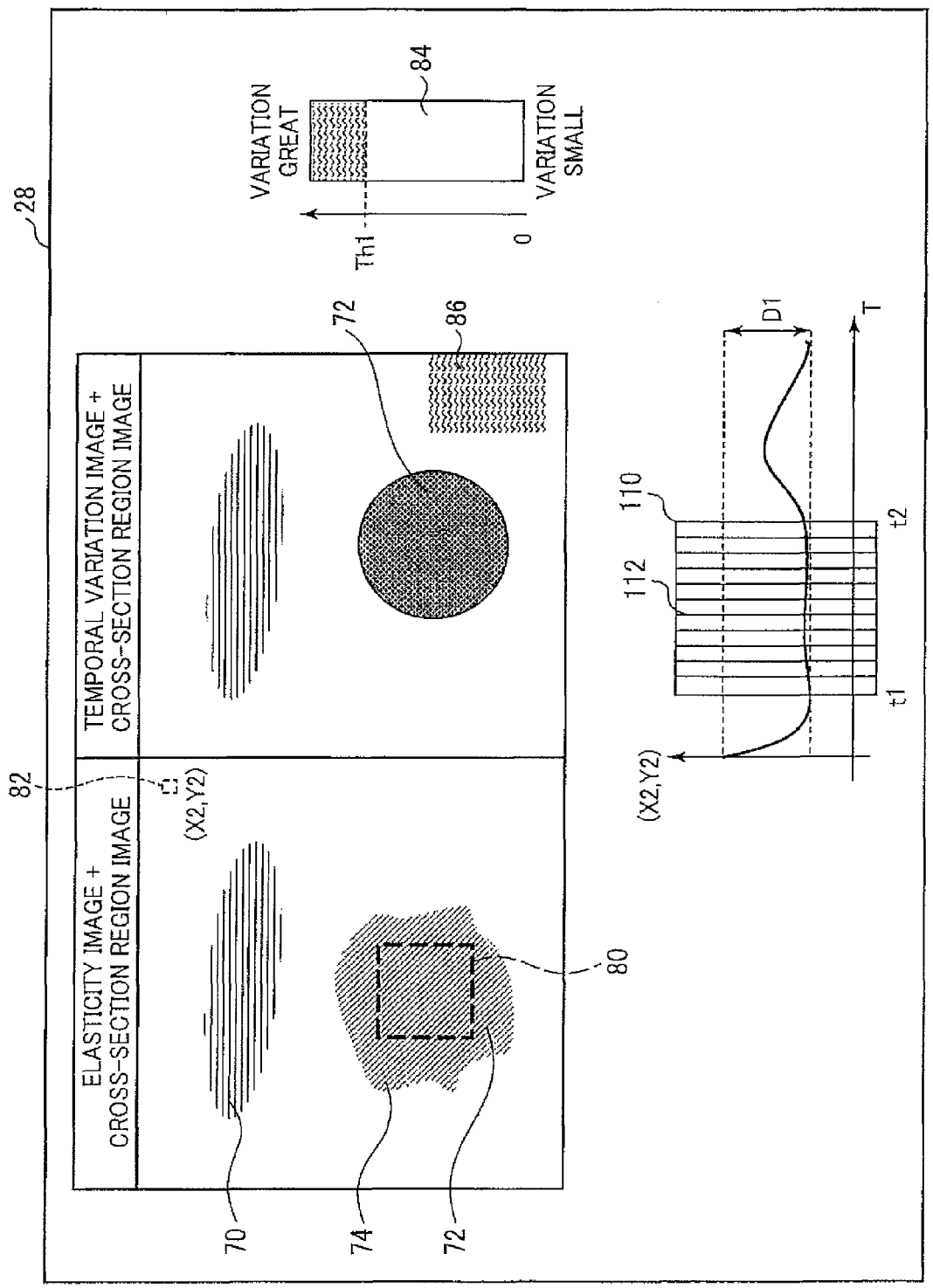
FIG. 7 is a diagram illustrating a display form of the image display unit of the present invention.

As illustrated in FIG. 7, the temporal variation calculating unit 62 of the temporal variation analyzing unit 50 calculates variation of the index value of the elasticity information (ratio of the elasticity information) at the respective measurement points in the plurality of frames of the elasticity information as described in the first embodiment.

As illustrated in FIG. 3, at the measurement points (X2, Y2), the difference D1 between the upper limit value and the lower limit value of the ratio of the elasticity information is greater than the predefined threshold Th1, and the variation of the ratio of the elasticity information is great. While the temporal variation calculating unit 62 calculates that the measurement points (X2, Y2) are measurement points at which the temporal variation is great, the index value is stable in a time period between time t1 and time t2. The time period between time t1 and time t2 during which the index value is stable is a time period during which the difference D1 between the upper limit value and the lower limit value of the ratio of the elasticity information is smaller than the predefined threshold Th1.

As illustrated in FIG. 7, the time period 110 between time t1 and time t2 is a time period during which the difference D1 between the upper limit value and the lower limit value of the ratio of the elasticity information is smaller than the predefined threshold Th1. That is, the time period 110 between time t1 and time t2 can be regarded as a time period during which the index value is stable. Therefore, the calculation time setting unit 100 selects the time period between time t1 and time t2 during which the index value is stable and sets the time period 110 between the time t1 and time t2 during which the index value is stable as calculation time of the calculation time setting unit 100. The image display unit 28 displays the time period 110 between time t1 and time t2 during which the index value is stable.

The elasticity information calculating unit 34 calculates an index value of the elasticity information in the time period 110 between time t1 and time t2 set by the calculation time setting unit 100. It is also possible to select a plurality of frames from the time period between time t1 and time t2 and calculate an index value of the elasticity information in the selected frames 112. The image display unit 28 displays the selected frames 112.

The elasticity information calculating unit 34 can calculate an index value of the elasticity information according to the number of frames if the number of frames to be selected from the time period between time t1 and time t2 is determined in advance. For example, if the number of frames is set at ten, it is possible to select ten frames from the time period between time t1 and time t2, and the elasticity information calculating unit 34 can calculate an index value of the elasticity information from the selected ten frames.

According to the present embodiment, it is possible to calculate an index value of the elasticity information at a stable measurement position in a region other than the region where the temporal variation image is displayed and during the time period during which an index value is stable. That is, it is possible to calculate an index value of the elasticity information at a stable measurement position without depending on the operator.

REFERENCE SIGNS LIST

10 Diagnosing object
12 Ultrasound probe
14 Transmitting unit
18 Ultrasound transmission and reception control unit
20 Receiving unit
22 Phasing and adding unit
24 Cross-section region image constituting unit
26 Image synthesizing unit
28 Image display unit
30 RF signal frame data selecting unit
32 Displacement measuring unit
34 Elasticity information calculating unit
36 Elasticity image constituting unit
40 Operating unit
42 Control unit
50 Temporal variation analyzing unit
52 Temporal variation image constituting unit
60 Elasticity information frame storing unit
62 Temporal variation calculating unit

The invention claimed is:

1. An ultrasonic diagnosis apparatus comprising:
a cross-section region image constituting unit that, when executed by a processor, constitutes a cross-section region image of a diagnosis portion of a diagnosing object through an ultrasound probe;
an elasticity information calculator that calculates elasticity information indicating hardness;
an elasticity image constituting unit that, when executed by a processor, constitutes an elasticity image based on the elasticity information calculated at the elasticity information calculator;
an image display that displays the cross-section region image and the elasticity image;
a temporal variation analyzing unit that, when executed by a processor, analyzes temporal variation at respective measurement points from the elasticity information calculated at the elasticity information calculator;
a temporal variation image constituting unit that, when executed by a processor, constitutes a temporal variation image based on the temporal variation analyzed at the temporal variation analyzing unit,
wherein:
the temporal variation image constituting unit constitutes the temporal variation image for a measurement point at which the temporal variation is greater than a threshold, and does not constitute the temporal variation image for a measurement point at which the temporal variation is smaller than the threshold, and
the image display displays the temporal variation image.

2. The ultrasonic diagnosis apparatus according to claim 1, wherein the temporal variation analyzing unit comprises:
an elasticity information frame storing unit that, when executed by a processor, stores plurality of frames of elasticity information; and
a temporal variation calculator configured to calculate temporal variation from the plurality of frames of the elasticity information.

3. The ultrasonic diagnosis apparatus according to claim 2, wherein the temporal variation calculator calculates the temporal variation using any one of a ratio, a difference, standard deviation, dispersion and a coefficient of variation of the elasticity information.

4. The ultrasonic diagnosis apparatus according to claim 2, wherein the temporal variation calculator calculates an index value of the elasticity information at a region of interest and respective measurement points set in a synthetic image of the cross-section region image and the elasticity image in the plurality of frames of the elasticity information and calculates variation of the index value of the elasticity information at the respective measurement points.

5. The ultrasonic diagnosis apparatus according to claim 2, wherein the temporal variation calculator calculates a difference between an upper limit value and a lower limit value of a ratio of the elasticity information at the respective measurement points in the plurality of frames of the elasticity information, and, when the difference between the upper limit value and the lower limit value of the ratio of the elasticity information is greater than a predefined threshold, calculates that temporal variation is great.

6. The ultrasonic diagnosis apparatus according to claim 2, wherein, when the difference between the upper limit value and the lower limit value of the ratio of the elasticity information is greater than the predefined threshold, the temporal variation image constituting unit constitutes the temporal variation image and makes the image display displays the temporal variation image.

7. The ultrasonic diagnosis apparatus according to claim 2, wherein, when displacement of the elasticity information is greater than a predefined threshold, the temporal variation calculator calculates that temporal variation is great.

8. The ultrasonic diagnosis apparatus according to claim 1, wherein the image display displays a synthetic image of the cross-section region image and the temporal variation image.

9. The ultrasonic diagnosis apparatus according to claim 1, further comprising a controller configured to control the image display to display an alarm for shooting an image again when the temporal variation image is equal to or greater than a predetermined region.

10. The ultrasonic diagnosis apparatus according to claim 1, further comprising a controller configured to recognize a region where the temporal variation image is displayed and set a region other than the region where the temporal variation image is displayed as a region of interest.

11. The ultrasonic diagnosis apparatus according to claim 1, wherein a first region of interest and a second region of interest are set in advance, and, when the temporal variation image constituted by the temporal variation image constituting unit is superimposed on the first region of interest and the second region of interest, the elasticity information calculator does not calculate an index value of the elasticity information in the first region of interest and the second region of interest.

12. The ultrasonic diagnosis apparatus according to claim 1, further comprising a calculation time setting unit that, when executed by a processor sets a calculation time during which an index value of the elasticity information is calculated at the elasticity information calculator.

13. An image display method for displaying a cross-section region image and an elasticity image, the method comprising:
analyzing temporal variation at respective measurement points from elasticity information indicating hardness;
constituting a temporal variation image based on the temporal variation;
constituting the temporal variation image for a measurement point at which the temporal variation is greater than a threshold and does not constitute the temporal variation image for a measurement point at which the temporal variation is smaller than the threshold; and
displaying the temporal variation image.

14. An ultrasonic diagnosis apparatus comprising:
a cross-section region image constituting unit, executed by a processor, to constitute a cross-section region image of a diagnosis portion of a diagnosing object through an ultrasound probe;
an elasticity information calculator that calculates elasticity information indicating hardness;
an elasticity image constituting unit, executed by a processor, to constitute an elasticity image based on the elasticity information calculated at the elasticity information calculator;
an image display that displays the cross-section region image and the elasticity image;
a temporal variation analyzing unit, executed by a processor, to analyze temporal variation at respective measurement points from the elasticity information calculated at the elasticity information calculator;
a temporal variation image constituting unit, executed by a processor, to constitute a temporal variation image based on the temporal variation analyzed at the temporal variation constituting unit,
wherein a first region of interest and a second region of interest are set in advance, and, when the temporal variation image constituted by the temporal variation image constituting unit is superimposed on the first region of interest and the second region of interest, the elasticity information calculator does not calculate an index value of the elasticity information in the first region of interest and the second region of interest, and
wherein the image display displays the temporal variation image.

* * * * *